United States Patent [19]

Range

[11] 4,131,426
[45] Dec. 26, 1978

[54] TIP WIPER APPARATUS AND METHOD

[75] Inventor: Richard J. Range, Silver Spring, Md.

[73] Assignee: Baxter Travenol Laboratories, Inc., Deerfield, Ill.

[21] Appl. No.: 827,221

[22] Filed: Aug. 24, 1977

[51] Int. Cl.² .............................................. G01N 1/14
[52] U.S. Cl. ........................................ 141/1; 15/246; 141/130; 422/100
[58] Field of Search ................. 23/259, 230 R, 253 R; 15/246

[56] References Cited

U.S. PATENT DOCUMENTS

| 3,753,657 | 8/1973 | Downing et al. ................. 23/253 R |
| 3,768,526 | 10/1973 | Sanz et al. .......................... 23/253 X |

Primary Examiner—R.E. Serwin
Attorney, Agent, or Firm—Henry W. Collins; James T. Fitzgibbon; George H. Gerstman

[57] ABSTRACT

An apparatus for wiping the tip of a sample dispensing tube. The apparatus includes means such as a pair of arms for locating the tip portion of a dip tube and for guiding the tube for movement between a first operative position in which the tube aspirates a charge of liquid from a sample container and a second position in which said tube will discharge said liquid into a reaction vessel such as a transfer disc. The wiper includes means for receiving a supply of absorbent wiping material in ribbon form, and a spool for taking up the ribbon, as well as means defining a path along which said ribbon will move between the supply means and the takeup spool. A pair of pins or the like are spaced closely apart from said tip and adapted to urge said ribbon into wiping contact with said tip. The takeup spool is driven in response to movement of the locating and guiding arms. Clutches or the like are provided for maintaining said ribbon under tension while the ribbon moves along its path, and in use, the ribbon is advanced from the supply means and wound upon the takeup spool, while being wiped along the tip of the tube during movement of the arm between its first and second positions.

15 Claims, 11 Drawing Figures

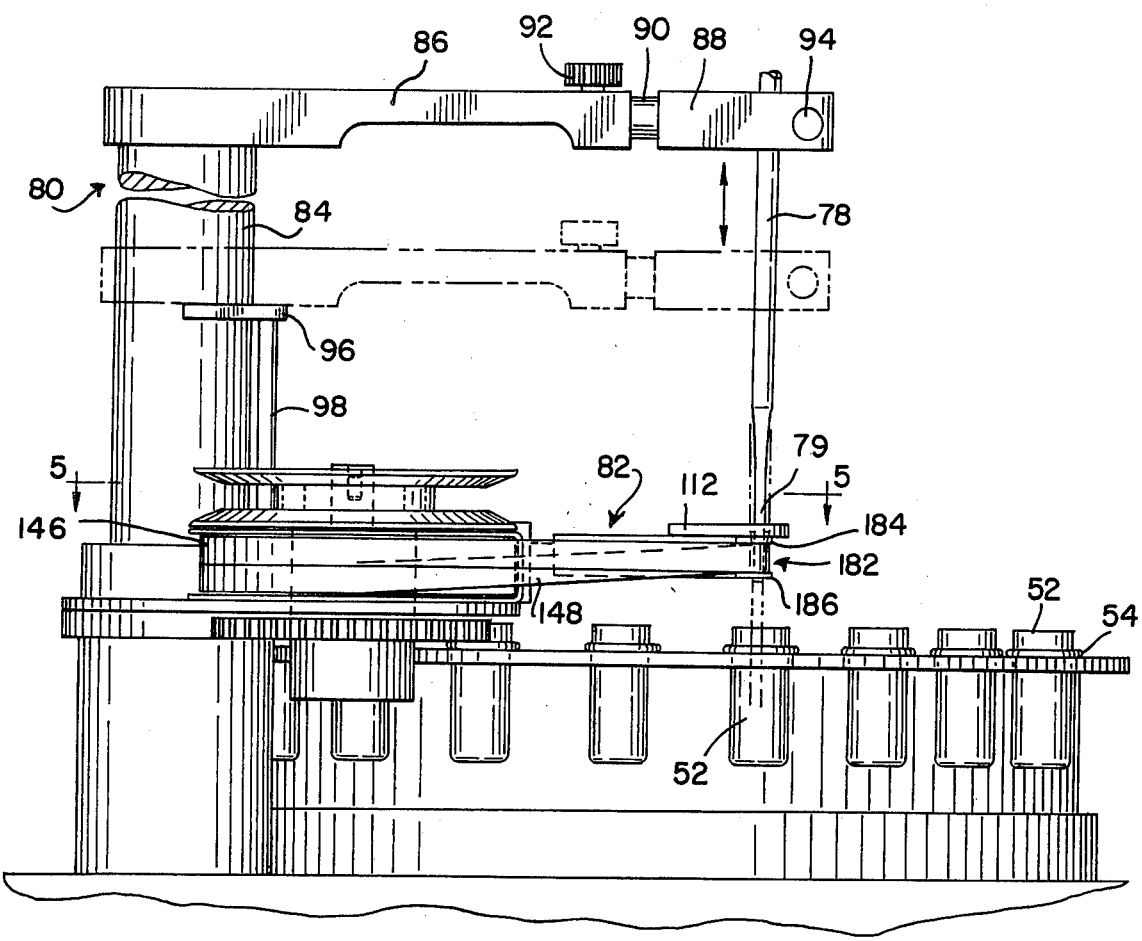
FIG_3_
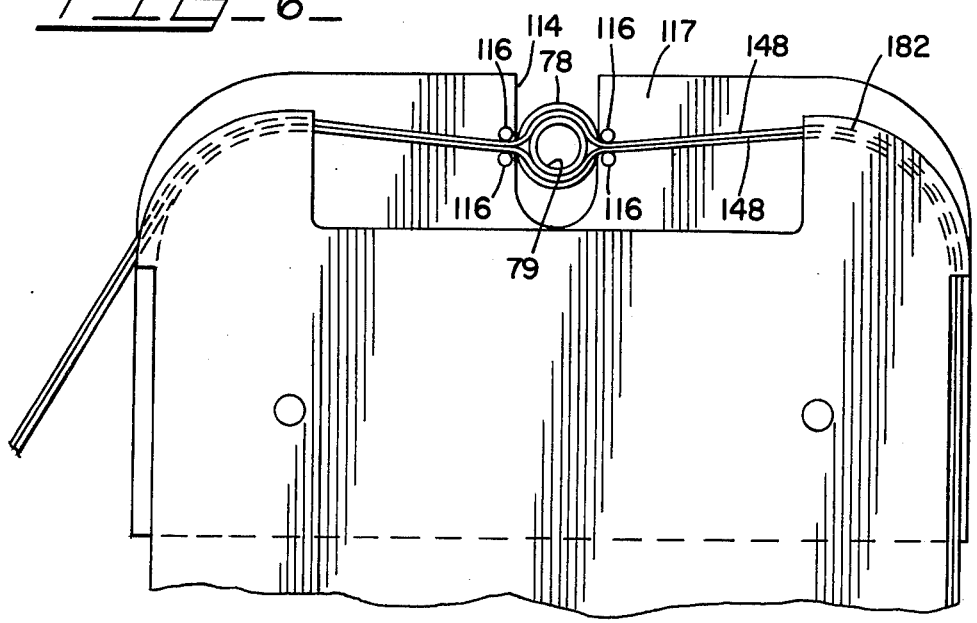
FIG_6_

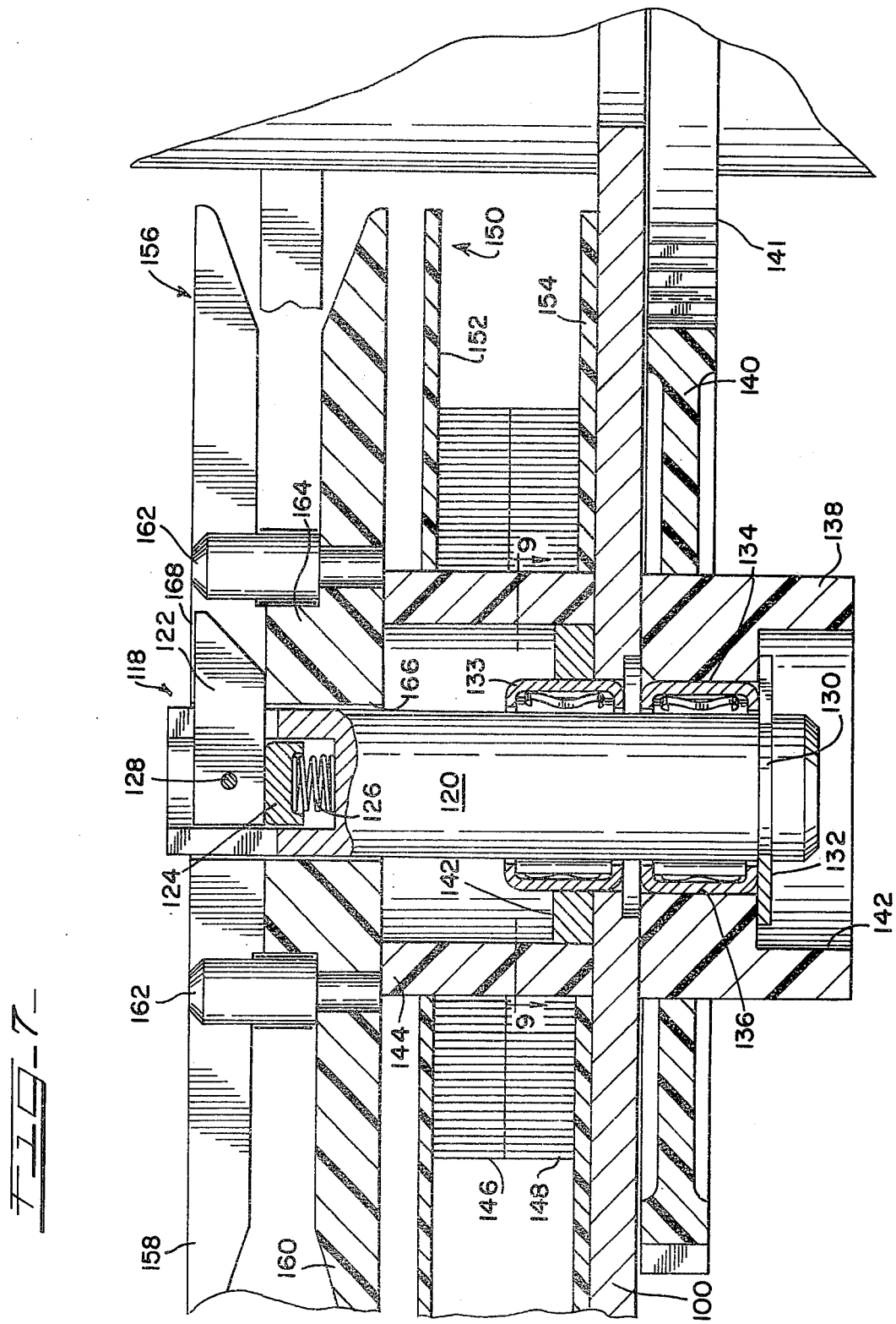

TIP WIPER APPARATUS AND METHOD

BACKGROUND OF THE INVENTION

The present invention relates generally to laboratory apparatus, and more particularly to an improved reagent or specimen filler which includes means for automatically wiping excess reagent from the liquid transfer tube used to measure and transfer the reagent between containers in automated analysis equipment. The present invention provides a tip wiper construction which is compatible with both rigid and resilient transfer tube tips and which avoids the shortcomings of prior art tip wiper devices and methods of the prior art.

In modern laboratory analysis, including analysis of blood serums, for example, it is very common to use sophisticated electronic equipment which is capable of analyzing such specimens before, during, or after such specimens undergo a chemical reaction with known reagents. Such analysis is typically carried out by projecting one or more light beams through a container having therein a laboratory sample, and then measuring certain physical characteristics of the specimen, such as absorption of a characteristic light frequency band, scattering of light by the specimen, or other physical phenomena.

Typically, such analysis instruments are capable of determining the presence of certain components, the concentration of such components, as well as analyzing certain characteristics of the reaction between the specimen being analyzed and standard reagents. Instruments of this type are capable of analyzing a large number of specimens in a short time with a high degree of accuracy; however, in many cases the accuracy potential of the instrument used for analysis cannot be achieved because of the presence of random error in sampling.

In other words, where the specimen itself is not capable of, or is not in fact, being handled with a given degree of accuracy, the use of a machine capable of a much higher order of accuracy is not necessary, and in some cases, may create an implication of higher accuracy than can, in fact, be attained where the samples are not accurately taken.

In a number of laboratory analysis processes, one problem is that of cross-contamination between various specimens. In other words, where a number of specimens are to be withdrawn from different containers and placed in analysis vessels, it is necessary that substantially no portion of the specimen taken from one container be introduced into another or different container. This commonly happens in laboratory equipment wherein a pipette, a dip tube, or the like is used to aspirate or withdraw the specimen from a container. Where specimens are individually pipetted, the pipette or dip tube can be cleaned by the operator. However, the speed potential of any such operation requiring repeated attention by humans is very low. On the other hand, the use of automated equipment commonly involves using the same dip tube for a plurality of specimens, and the potential for contamination between successive specimens is always present, and in certain cases, may be harmful to the accuracy of the process or may make impossible the achievement of the accuracy which the process is otherwise capable of achieving.

Accordingly, it is desired that liquid handling equipment be provided which is capable of both the speed and the accuracy potential of modern laboratory analyzers. An ideal instrument for this purpose would be one which would provide a simple and effective means of wiping excess fluid from the tip of each tube which is immersed in a laboratory specimen for the transfer of a portion thereof to an analysis vessel before the tip portion contacts the liquid in a subsequent storage vessel.

Such an ideal apparatus would be compatible with existing equipment, would include simple and effective means for wiping the tip, and could wipe the tip repeatedly without requiring attention from the operator. Ideally, the apparatus could also do so without compromising the accuracy of the measurements or imposing a physical strain on the apparatus.

In the prior art, the possibility of rinsing transfer tube tips has been considered; however, this method has certain drawbacks. Sometimes this process draws liquid from the tip, which is undesirable, and, also, rinsing requires that rinsing be carried out in an area remote from the transfer operation. It has also been proposed to dry the tips of such instruments by the use of compressed air or the like; this concept is also undesirable insofar as it may tend to disturb liquid in the interior of the tip, causing inaccuracies in volumetric measurements, and also raises the possibility of blowing droplets of liquid into other areas wherein contamination could occur.

Other proposals for tip wipers have included the provision of a sheet of paper which the tip is caused to pierce and move through; however, this is not always practical with relatively flexible tips made from plastic tubing, and, moreover, this concept potentially involves withdrawing a certain amount of fluid from the interior of tips by capillary action when the tube end meets the paper.

According to the present invention, an apparatus is provided, in a preferred form, wherein two rolls of a ribbon or tape-like absorbent paper or like material are held on reels in a supply area and trained by guide means into the vicinity of the tip, with additional means being provided for periodically advancing the ribbons from the supply reel onto a take-up reel and moving them across the tips with a wiping action each time the unit supporting the tip is moved between aspirating and discharge positions with respect to specimen and analysis containers respectively.

In view of the shortcomings of prior art devices, and the need for an improved tip wiper apparatus, it is an object of the present invention to provide an improved tip wiper apparatus.

Another object is to provide an apparatus which includes means for receiving and taking up a supply of tip wiping material in ribbon form, and which will be actuated upon movement of the tip between different operative positions thereof.

Yet another object is to provide an apparatus for wiping the tip of a specimen transferring pump apparatus which will aspirate and discharge specimens repeatedly without the need for frequent operator attention.

A further object is to provide a tip wiper apparatus which is capable of wiping the tip of a liquid transfer tube or the like without damaging the tip and without undesirably withdrawing fluid from the inside thereof.

A still further object is to provide a tip wiper apparatus which includes a pair of supply reels for tip wiping material and a take-up spool for spent material, and which can be operated in a positive manner so as to wipe the tip without requiring the additional motion devices or motion sequences in the analysis device with which the tip wiper is associated in use.

Another object is to provide a tip wiper apparatus which includes supply and take-up reels for the tip wiper material, with such reels being operated through an overrunning or other one-way clutch arrangement so as to provide positive advancement of the tip wiper material and to avoid the creation of slack or backlash in the operating unit.

A further object is to provide a tip wiper unit which includes means for supplying and taking up tip wiping material in ribbon form and which includes guideways adapted to direct material from a pair of axially spaced reels onto a common path, to guide the ribbons of material past the tip in the vicinity thereof, and to guide the material towards the take-up reel thereafter.

A still further object is to provide a tip wiper which can be used with a variety of units and which requires no additional equipment to be installed and synchronized with existing equipment.

Another object is to provide a tip wiper unit which is compatible with existing equipment and which will permit a full, uninterrupted range of tip movement without damage to the unit.

Yet another object is to provide a tip wiper unit which is capable of being supplied periodically with new reels or containers of ribbon with a minimum of difficulty, and which is arranged for simple and straightforward feeding of such material.

A still further object is to provide a tip wiper which will permit axial reciprocation of the tube while locating the tube between guide means while wiping takes place.

These and other objects of the invention are achieved in practice by providing a tip wiping apparatus which includes means adapted to receive an aspiration and discharge tip, means for receiving a supply of unused tip wiping material and for taking up a supply of used tip wiping material, means for guiding the material into the vicinity of and across portions of the tip with an effective wiping action, and means for providing an intermittent advancing motion to the wiping material so as to move it past the tip in response to movement of the tip between aspiration and discharge positions.

The exact manner in which these and other objects and advantages are achieved in practice will become more clearly apparent when reference is made to the following detailed description of the preferred embodiments of the invention set forth by way of example and shown in the accompanying drawings, in which like reference numbers indicate corresponding parts throughout.

BRIEF DESCRIPTION OF THE DRAWINGS

FIG. 1 is a perspective view of a filling apparatus embodying the tip wiper of the present invention and showing the analysis receptacles, an indexed carrier for specimens, and a so-called transfer disc which is adapted for subsequent insertion into a multi-channel photometric analyzer or the like;

FIG. 3 is an enlarged side elevational view, with portions broken away, taken along lines 3—3 of FIG. 2, and showing the relation of the tip wiper assembly to the arm and related mechanism for manipulating the tube having the tip to be wiped;

FIG. 6 is a further enlarged fragmentary bottom plan view, taken along lines 6—6 of FIG. 4, and showing the construction features of the ribbon guide and tip-receiving slot;

FIG. 7 is a further enlarged vertical sectional view, taken along lines 7—7 of FIG. 4, and showing the supply and take-up reels, and the drive and clutch mechanism associated therewith;

DESCRIPTION OF THE PREFERRED EMBODIMENTS OF THE INVENTION

While it will be understood that the principles of the present invention are applicable to different forms of apparatus, a description of a preferred form of the invention will be given wherein the tip wiper of the invention is associated in use with an automatic sample and reagent transfer apparatus.

More specifically, the present invention is typically used in association with an automatic sample and reagent dispenser which preferably includes two double pumps and which is adapted to pick up and transfer a pre-selected portion or aliquot of serum, standard, control, or blank from a container received in a rotary carrier and dispensing this aliquot into a transfer disc having a plurality of individual wells therein. In addition, the unit dispenses one or two reagents into the transfer disc, and dispensing the serum or the like may also be followed by a rinse of water or other diluent. The reagent volumes are selected by appropriate control of the transfer instrument. After the wells are filled with sample, reagent, and/or diluent, the transfer disc is placed into a multi-channel photometric analyzer wherein kinetic rate measurements of enzyme activity or end-point determinations of metabolites may be taken. Such analyzers are commonly also equipped with small programmable computers, and are able to be instructed or programmed to perform desired analysis operations and furnish data as desired by the operator. While the exact function of such apparatus does not form a part of the invention, reference is made thereto to emphasize the importance of accuracy in making the initial measurements of reagent. With analysis of such a high degree of accuracy being able to be performed, it is further desirable that there is no cross-contamination of specimens, and that each sample or specimen is measured as accurately as possible.

In one form of sample dispenser, the reagent tube is supported by an arm which oscillates between pickup and discharge areas. According to the invention, advantage is taken of this oscillating movement to advance the tape or ribbon of absorbent material from the ribbon supply area to the take-up area. The arm used to locate the pickup and discharge tube is used to guide the wiping tape into a position adjacent the tip where additional guide means are provided to insure proper pressure and duration of contact between the ribbon or tape and the tip of the tube. The lower edge of the ribbon is spaced just far enough from the end of the tip so that it does not withdraw the contents of the tube by capillary action.

Figure 1:
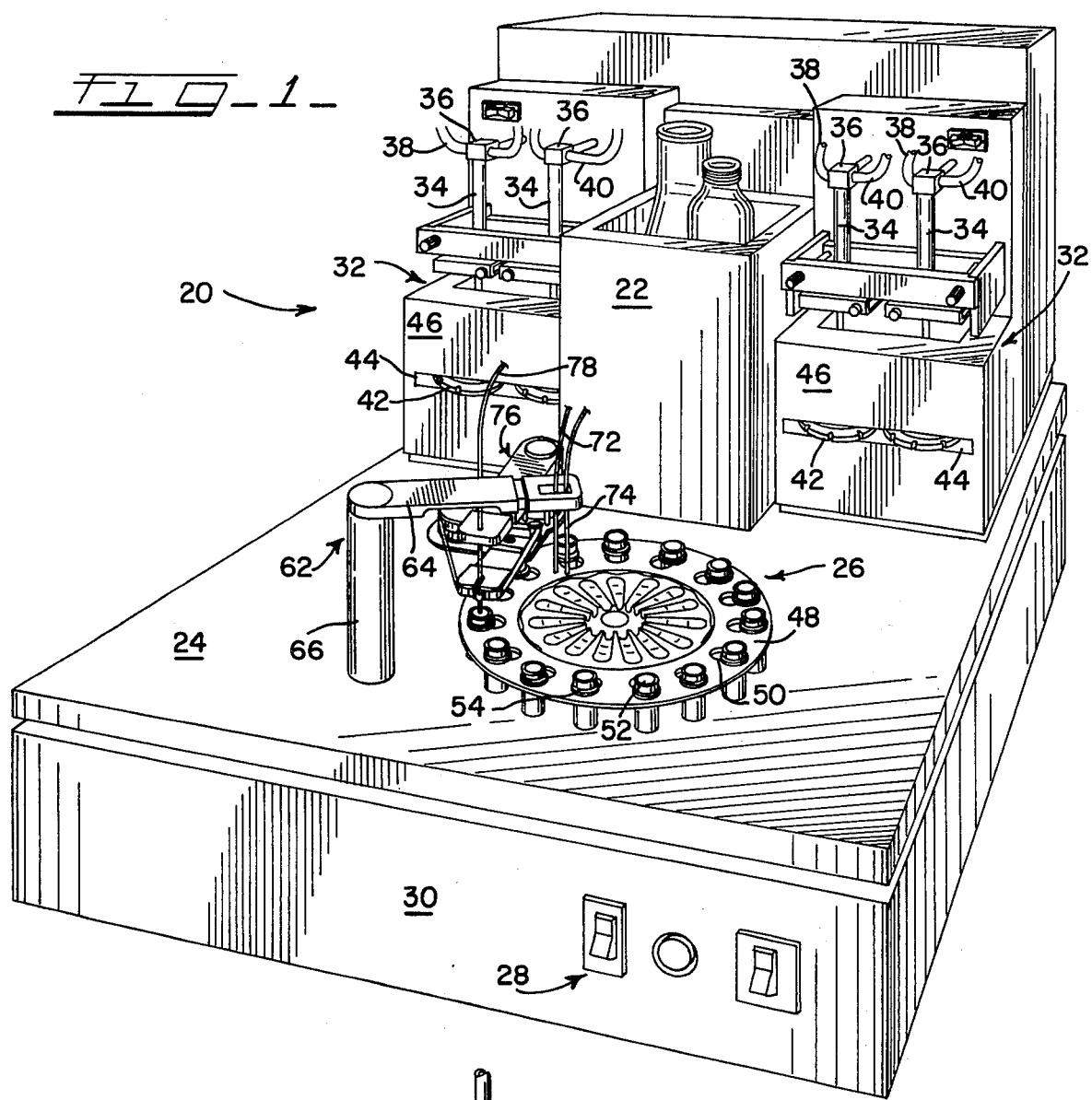
Figure 4:
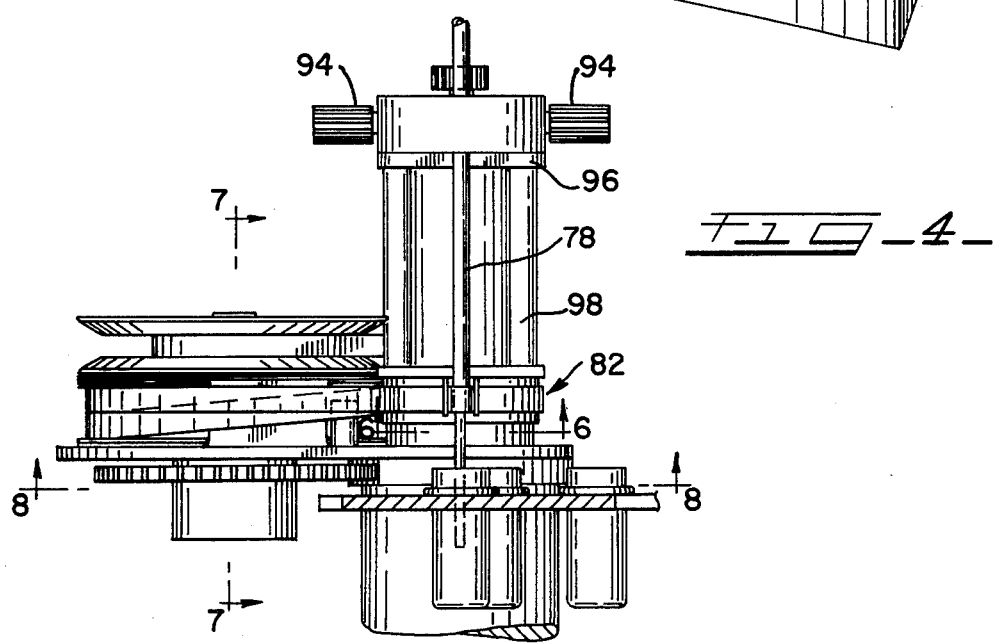
FIG. 4 is a side view taken along lines 4—4 of FIG. 2, partly in section and partly in elevation, and showing the tip wiper apparatus and the positions of the supply and take-up reels for the wiping material as well as the positions of the tube and tip thereof relative to the sample carrier.

Referring now to the drawings in greater detail, one form of automatic dispenser and transfer apparatus generally designated 20 is shown in FIG. 1, and is shown to include a housing 22 for reagent bottles, and a generally horizontally extending forward deck 24, which in turn supports a turntable assembly 26 to be described in detail herein. Controls, switches and the like 28 are disposed on the forward wall 30 of the deck 24 for manipulation and observation by the user. The unit 20 also includes a pair of double pump housings 32 each receiving therein a positive displacement pump, each of which, in turn, is shown to include a cylinder 34 and a flow control valve 36. Typically, each pump withdraws a fluid through one of the lines 38 and discharges it into another line 40 under control of the valve 36.

The quantity of liquid discharged through the lines 40 is determined by manipulation of the volume control dials 42 which are accessible to the operator through slots 44 in the lower cabinet portions 46 serving to house the other pump elements. For ease of understanding, the connections between the lines 40 and the counterpart tubes of the apparatus are not shown, it being understood that such connections are made in a manner known to those skilled in the art to insure that the various reagents and/or diluents are supplied to the desired positions within the transfer disc before it is removed from the apparatus for insertion into the photometric analyzer.

Figure 2:
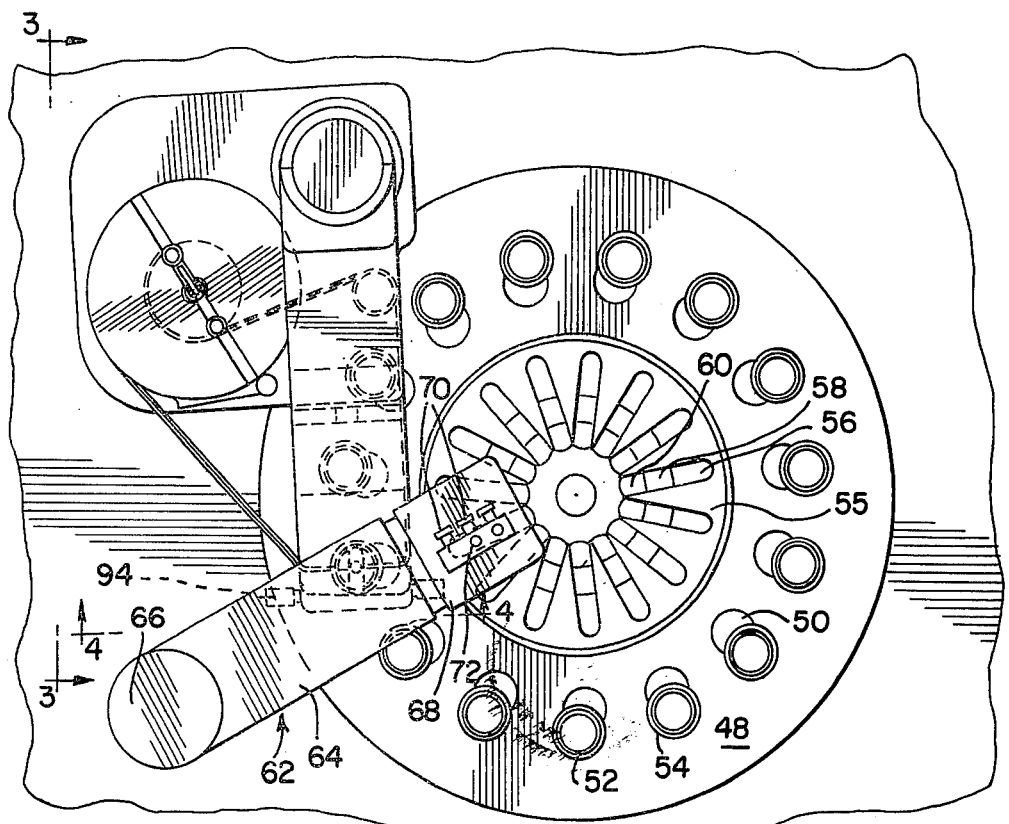
FIG. 2 is a plan view, with portions broken away, on an enlarged scale, showing the tip wiper apparatus, including the holder frame for the spools and the aspirator tube, with a portion thereof shown disposed in position of use over the indexed carrier for specimens.
Figure 5:
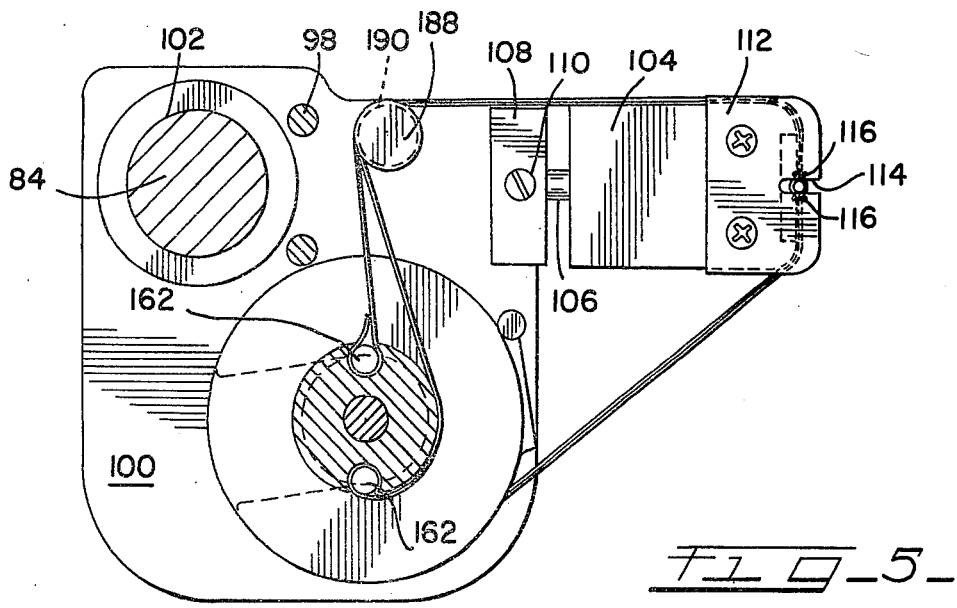
FIG. 5 is a horizontal sectional view, taken along lines 5—5 of FIG. 3, and showing the path of the ribbon of the tip wiper material from the supply reel around the guides, across the tip, and onto the take-up reel.

Referring again to FIGS. 1 and 2, the turntable assembly 26 is shown to include a container-receiving ring 48 which includes a plurality of elongated slots 50, each of which may receive a container 52 designed so as to include an annular mounting shoulder 54. Inside the container ring 48 is a transfer disc generally designated 55 and shown to include a plurality of sets of individual wells, including a radially outer well 56, an intermediate well 58 and a radially inner well 60. During processing, the liquid moves from the inner well to the intermediate and finally the outer well as the liquid is mixed and subsequently analyzed in a reaction cuvette or like chamber (not shown) outboard of the outermost well 56.

Other principal components of the invention include a diluent feed assembly, generally designated 62, which is adapted to feed diluent and/or reagents respectively to one or more of the wells 56–60 for mixing and reaction with the serum removed from each individual container 52. The diluent feed assembly includes a tube locating arm 64, an arm support post 66, and a tube-aligning head 68 which includes means in the form of set screws 70 or the like to assist in locating diluent/reagent tubes 72 extending therethrough and having their end portions 74 (FIG. 1) extending downwardly into positions adjacent the wells 56–60.

In the normal use of the form of apparatus shown, the diluent feed assembly furnishes diluents and/or reagents into the wells but does not serve the function of transferring different serum samples and, accordingly, the arm 64 remains fixed in the position shown and does not normally move during use.

Referring now to another assembly, namely, the liquid aspiration or pickup and/or discharge apparatus generally designated 76 in FIGS. 1–4, the main components of this assembly 76 include an aspiration and discharge tube 78, a portion generally designated 80 (FIG. 3) for reciprocating the tube 78, and a ribbon feed and take-up assembly generally designated 82. In use, the tube reciprocating assembly moves in such manner that the tube tip 79 is first moved into the serum container, then raised upwardly therefrom, and is then lowered into an appropriate well 56, wherein the contents of the tube are discharged. In a related movement sequence, a portion of the ribbon feed and take-up assembly 82 oscillates through an arc in such a manner that the tube 78 is positioned above a container 52 for aspiration and above the well 56 for discharge. The tip wiper of the invention permits the tip portion 79 of the tube 78 to be wiped automatically under controlled conditions at this time, as will be described in detail herein.

Referring again to the sample tube reciprocating assembly 80, this unit is shown in FIG. 3 to include a vertically reciprocable post 84 and a transfer tube support arm 86 having a head portion 88 which is affixed to the arm 86 by a shaft 90 which is in turn located by a thumb screw 92. Means in the form of a knob 94 is provided for securing the tube 78 in place within the head 88. It will be understood that vertical reciprocation of the post 84 may be accomplished by a cam drive or like known mechanisms (not shown), which does not form a necessary part of the invention, and which is therefore not described in detail herein.

Typically, the arm 86 is reciprocated through a distance such as that indicated in phantom lines in FIG. 3; the downward movement of the arm 86 is limited by a stop collar 96 extending between a pair of posts 98 extending upwardly from the ribbon feed and take-up assembly 82.

Referring now to the details of the feed and take-up assembly 82, this unit will be seen to include means in the form of a spool mounting plate 100 having an opening 102 therein for receiving the post 84 in guiding relation. A tube tip and ribbon guide arm 104 is attached, as by an adjustable shaft 106, to a holder 108 where it is secured by a fastener 110 to the plate 100. The arm 104 includes a cover plate 112 with a tube tip guide slot 114 found in the end thereof and with pairs of ribbon or tape guide pins 116 referred to elsewhere herein extending downwardly therefrom.

The spool support plate portion 102 of the ribbon feed and take-up assembly 82 includes a drive shaft assembly generally designated 118 and, as best shown in FIG. 7, the assembly 118 includes a central shaft body portion 120, a take-up spool-engaging key 122, and a plunger 124 loaded by a spring 126 to permit pivotal movement of the key 122 about the pin axis of the pivot pin 128. The shaft 120 also includes a groove 130 spaced apart from the lower end thereof and adapted to receive a nap ring 132 therein.

The shaft assembly 118 is received within one-way drive means comprising an upper clutch 133 and a lower clutch 134, with the lower clutch 134 being received in an opening 136 in a hub element 138, the outer periphery of which snugly engages an axle drive ring gear 140. The ring drive gear 140 has teeth engaging the teeth on a drive gear sector 141.

A counterbore 142 in the hub 138 accommodates the snap ring 132 which limits the upward movement of the drive shaft 120. The shaft 120 extends through the plate 100 and also engages the upper clutch 133 received within the clutch retaining collar 143. A hub 144 is arranged concentrically of the collar 143 and serves to locate the upper and lower rolls 146, 148 of ribbon held in a clip 150 having upper and lower surfaces 152, 154.

The exterior casing of the clutch 133 is secured against movement relative to the plate 100 by being pressed snugly within an opening therein. Disposed atop the rolls 146, 148 of ribbon and resting upon the upper surface of the hub 144 is a take-up spool generally designated 156. This spool includes upper and lower flanges 158, 160, a pair of identical pins 162 adapted to secure the ends of the ribbons, and a take-up spool hub 164 disposed centrally thereof and including a center bore or opening 166. A slot portion 168 is provided in the take-up spool to receive the key 122 which insures that the spool 156 will rotate with the shaft or axle 120.

Figure 9:
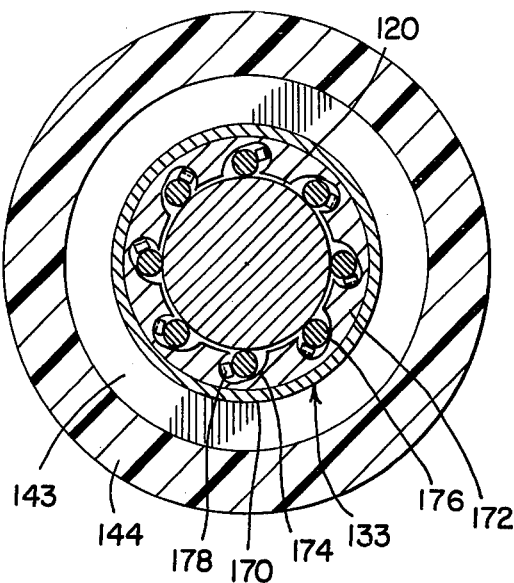
FIG. 9 is a horizontal sectional view of one of the overrunning clutch mechanisms of the invention, taken along lines 9—9 of FIG. 7.

Referring again to the drive mechanism for the axle 120, a typical clutch assembly generally designated 133 is shown in enlarged form in FIG. 9 to include an exterior housing or shell 170 which is received snugly within the collar 143 in the spool hub 144. The clutch itself is a typical one-way or overrunning clutch having a cage unit 172 with plural eccentric slots 174 therein for receiving rollers or pawls 176, urged as by spring means 178, toward the inside diameter of the clutch assembly and into engagement with the outer diameter of the shaft 120.

As is well known to those skilled in the art, the pawls become wedged in the taper between the case and the shaft or other relatively rotatable surface upon relative rotation in one direction, while relative rotation in the other direction urges the pawls or rollers into the recess or slots 174 against the force exerted by the springs 178. The springs 178 insure that the pawls or rollers 176 remain in contact with the engaged surface so that the clutch will actuate or hold with minimum back rotation.

The other clutch unit 134 is identical to the unit 133 except that it is installed upside down so that the taper in the slots extends clockwise, as opposed to the counterclockwise taper of the slots in the clutch unit 133.

Figure 8:
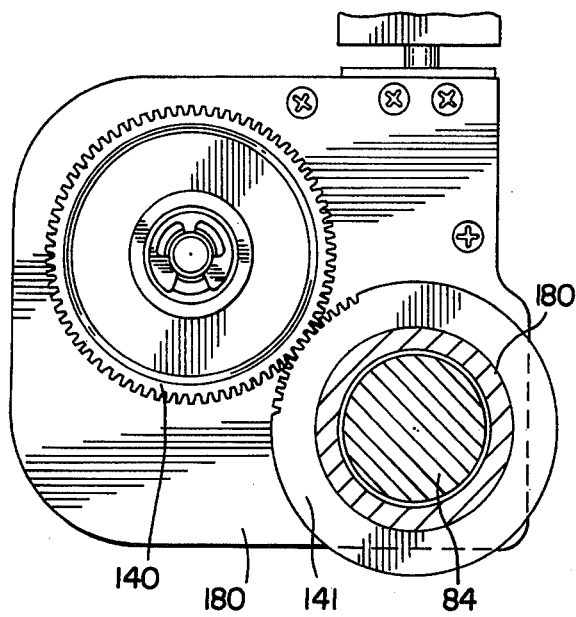
FIG. 8 is a horizontal sectional view, looking upwards along line 8—8 of FIG. 4, and showing additional details of the take-up reel drive mechanism.

Referring now to FIG. 8, it will be seen that the partial gear or sector 141 is also concentrically arranged with respect to the post 84 and it will be understood that the collar 180 and the sector 141 are locked together and against movement with respect to the frame of the machine. The collar 180 and gear 141 remain fixed with respect to the machine, while the plate 100 and the parts associated therewith pivot in use about the axis of the post 84. Pivoting or oscillating movement of the plate 104 causes rotation of the ring gear 140, moving it clockwise as seen from the bottom when the plate 100 also moves clockwise when similarly viewed. Thus plate oscillation causes intermittent rotation of the shaft 120.

Referring now to FIGS. 3-7, a typical installation is shown in which two ribbons of tape 146, 148 are superimposed in spool form over the hub 144, with the lower tape being drawn outwardly and upwardly toward a guide channel generally designated 182 and formed by upper and lower ribs 184, 186 disposed beneath the cover plate 112 on the arm 104. As shown in FIG. 6, the ribbons 146, 148 are then threaded between the guide posts 116 in such a manner that when the ribbons are maintained under tension they are trained over and nearly around a major part of the exterior surface of the tip 79, in close wiping contact therewith. A portion of the path to the take-up spool is also defined by a guide post 188 (FIG. 5) having a slot 190 therein over which both ribbons pass. The leading end of each ribbon is then trained over the pegs 162 as shown. Because the lower clutch locks the ring gear to the shaft 120, and because the upper clutch locks the shaft between rotation in the other direction relative to the plate, tension is always maintained on the ribbons, to urge them against the tip 79, an important feature of the invention. While the gear 140 undergoes intermittent motion, rotating the shaft somewhat each time the plate 100 is moved, the shaft 120 does not move or "float" backwardly with the drive gear because such movement is prevented by the upper clutch 133.

Figure 10:
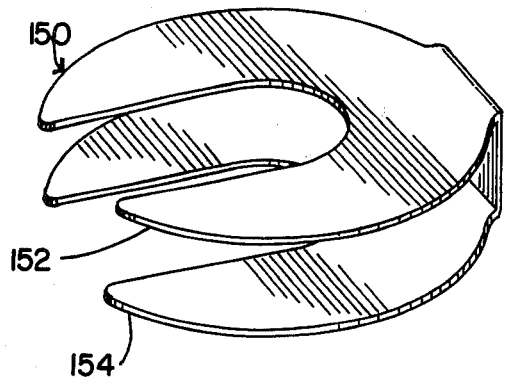
FIG. 10 is a perspective view of one of the tape holders of the invention before insertion of a roll of tape therein.
Figure 11:
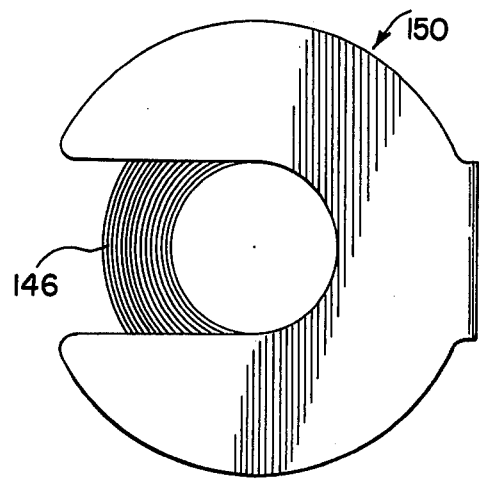
FIG. 11 is a top plan view of the tape holder of FIG. 10, showing the same with a supply of tape or ribbon received therein.

Referring now to FIGS. 10 and 11, details of the clip 150 used to store the ribbons are shown, with FIG. 11 showing the disposition of ribbons within the clip. This facilitates loading the apparatus, which is achieved by placing a pair of ribbons 146, 148 in superimposed relation between the upper and lower surfaces 152, 154 of the clip 150, and then inserting the clip over the hub 144. Thereafter the upper spool 156 is inserted in place and the key 122 is manipulated to lock the upper spool 156 in place; after the leading edges of the tapes or ribbons 146, 148 are trained over the posts 162, the tip wiper apparatus is ready to operate.

Referring now to the operation of the device of the invention, it will be assumed that the machine has been prepared for operation by disposing the ribbons of absorbent tape within the clip and loading the clip over the hub 144, with the ends of the tape being secured to the take-up spool 156 and with both tapes 146, 148 following the path from the from the supply spools defined by the channel 182 and trained around the tip 79 and between the guide pins 116, over the guide post 188 and to the take-up spool.

It will also be assumed that the containers 52 are filled with samples of blood serum and that the supply bottles in the cabinet 22 are filled with the reagents for analysis.

The tube 78 is locked in the head 88 of the upper support arm 86, and the arm 86 is in the upper or solid line position of FIG. 3. Thereupon, as the machine begins the operational sequence, the arm 86 is lowered, bringing the tip 79 of the tube 78 through the slot 114 in the cover plate 112 until the tip 79 is beneath the level of liquid in the container 52. The pump is then actuated so as to draw a measured quantity of the sample into the tube 78. Thereupon, the arm 86 is raised, bringing the tip 79 to its raised position lying within the slot 114 and with the lower end of the tip 79 extending just beneath the lower edge of the ribbons.

Both the arm 86 and the plate 100 containing the arm 104 are then swung as a unit radially inwardly of the turntable 26, aligning the tip 79 of the tube 78 in position over the outermost well 56. As the arm 104 is moved, the take-up spool is rotated by the action of the shaft 120 in response to movement of the ring gear 140, as referred to above. This advances the tapes and wipes any remaining sample liquid therefrom, advancing the dampened tape toward the take-up spool.

The arm 86 is then lowered again, and the contents of the tube 78 are pumped into the well 56. The arm 86 is again raised, and both it and the lower arm 104 are returned to their starting position for a repetition of this sequence.

In the meantime, while the contents of the tube 78 are being dispensed into the well 56, the other wells 58, 60 are being filled by action of the other pump withdrawing liquids from the containers in the cabinet 22 and forcing the liquids through the tubes or hoses 72, 74. If rinsing or purging is called for, it is also carried out at this point.

Because the reagents supplied through the tubes 72, 74 are the same in all cases, it is not necessary that there be a transfer of these quantities from individual containers to the well; the well is thus normally filled with a standard quantity of each reagent repeatedly. At the point in the sequence at which the wells are filled, the turntable is advanced one step and indexed so as to move the next succeeding container 52 beneath the tip 79. Thereupon, the tip is lowered, the second sample is aspirated, the tube 78 raised and withdrawn, and the sample is transferred. During angular movement of the arms, the tip 79 is again wiped by both tapes in the manner just described, and this sequence is repeated until such time as the transfer disc is entirely full, whereupon it is removed and placed in the photometric analyzer.

The wiping operation is conducted adjacent the work station of the tip, but there are no air blasts or other disturbing influences required, and the tip of the tube, which is normally of a relatively soft plastic material, is not required to pierce a paper or the like. The somewhat soft and flexible tip is supported against deflection by the removing and wiping by the edges of the slot 114 and by the guide pins 116.

The drive mechanism for oscillating the tube positioning arms between positions overlying the container ring 48 and the transfer disc is entirely conventional and may be a cam drive, a yoke arrangement, a crank mechanism or the like. Such drive units being commerically available and well known to those skilled in the art, and not forming a part of the invention which is novel per se, additional description thereof is unnecessary and will therefore be omitted.

In a typical apparatus, the tube 78 is a flexible plastic tube, with the tip 79 being of reduced diameter and drawn from the larger diameter portion in one piece. While part size or quantity is not a necessary feature of the invention, in a preferred form, the sample pickup volume is 5-50 microliters, the diluent volume 0-100 microliters and the reagent delivery volumes may be, for example, 0-500 microliters in the case of one pump and 0-200 microliters for the other pump.

Because the volume of the liquid clinging to the outside of the tip becomes larger in relation to the volume inside the tip as the tip diameter decreases, the increased importance of wiping when using small diameter tube tips will be appreciated. Accordingly, the invention is particularly advantageous when used with modern microanalysis equipment.

According to the present invention, the tip is always wiped with fresh paper, cloth, or the like, and the soiled ribbon is stored on the take-up reel for ready disposal after use. Although superimposing one supply of ribbon over the other causes one or both ribbons to be fed to the wiping area at a non-parallel angle, this arrangement has proved satisfactory in use and the two spool arrangement provides good tensioning and independent feed of the ribbon.

It will thus be seen that the present invention provides a novel tip wiping apparatus having a number of advantages and characteristics including those pointed out above and others which are inherent in the invention. A preferred embodiment of the invention having been described by way of illustration, it is anticipated that changes and modifications of the described tip wiping apparatus will occur to those skilled in the art and that such changes and modifications may be made without departing from the spirit of the invention or the scope of the appended claims.

I claim:

1. An apparatus for wiping the tip of a sample dispensing tube, said apparatus comprising, in combination, means for locating the tip portion of a dip tube and for guiding said tube for movement between a first operative position in which the tube will aspirate a charge of liquid and a second position in which said tube will discharge said liquid, means for receiving a supply of absorbent wiping material in ribbon form, means for taking up said ribbon, means defining a path along which said ribbon will move between said supply means and said take-up means, said path-defining means including means spaced closely apart from said tip and adapted to urge said ribbon into wiping contact with said tip, means responsive to said movement of said locating and guiding means for driving said take-up means, and means for maintaining said ribbon under tension while said ribbon moves along said path, whereby said ribbon is advanced from said supply means towards said take-up means, and wiped along the tip of said tube during movement between said first and said second positions.

2. An apparatus as defined in claim 1 in which said means for guiding said tube for movement between said first and second positions includes an arm mounted for pivotal movement, said arm having a slot therein for receiving the top of said tube, said slot permitting vertical movement of said tube but restricting lateral movement thereof parallel to or radially inwardly of the movement arc of said arm.

3. An apparatus as defined in claim 1 wherein said means for locating and guiding said tip comprises a first arm having a portion thereof secured to said tube and a second arm having a slotted end portion permitting relative vertical movement of the tip of said tube with respect thereto, said first and second arms being mounted for pivotal movement about the common axis.

4. An apparatus as defined in claim 1 which further includes a pair of substantially identical rolls of absorbent wiping material, said rolls being positioned one above the other for removal of ribbon therefrom by said takeup means.

5. An apparatus as defined in claim 1 in which said means for receiving said supply of wiping material includes a removable clip adapted to removably receive at least one roll of absorbent material.

6. An apparatus as defined in claim 1 wherein said receiving means and said means for taking up said ribbon comprises respectively, a pair of rolls of wiping material received for rotation with respect to said locating and guiding means, and a single takeup reel, said takeup reel including means for receiving the end portions of each of said wiping ribbons.

7. An apparatus as defined in claim 1 wherein said locating and guiding means includes a lower arm having a tip receiving slot therein, and wherein said means defining said ribbon path include a pair of channels formed in an end portion of said lower arm and located on either side of said slot, said path-defining means further including two pairs of pins extending parallel to and spaced just apart from the exterior surfaces of said tube tip, said pairs of pins being also spaced from said tip laterally of said slot so as to define the path of said ribbon to insure contact thereof with said tip.

8. An apparatus as defined in claim 1 wherein said takeup means is in the form of a single spool, said spool having means for receiving the end portions of said wiping material and further including means cooperating with said ribbon takeup driving means to provide readily removable engagement of said spool and said driving means.

9. An apparatus as defined in claim 1 wherein said locating and guiding means comprises a pair of arms, one being adapted to reciprocate for inserting and withdrawing said tube from a sample container in one position of said arm and for lowering said tube to a position adjacent a sample receiving vessel in another position of said arm.

10. An apparatus as defined in claim 1 wherein said locating and guiding means includes an arm mounted for pivotal movement with respect to a fixed portion of said apparatus, said means for driving said takeup means in response to arm movement including a gear sector fixed with respect to said arm, the peripheral portions of said gears being engaged in driving relation, a shaft extending axially of said rotatable gear, said shaft having a portion thereof removably received within said takeup means, and a drive connection between said gear and said shaft, said drive connection including a pair of clutches arranged for respective opposite hand engagement and release of said shaft, whereby said shaft and the takeup means associated therewith may be advanced by rotation of said gear in one direction and may be held against reverse rotation as said gear rotates in the opposite direction.

11. An apparatus for wiping the tip of a sample dispenser tube, said apparatus comprising, in combination, a frame unit and a first arm unit having a portion adapted to receive a dispensing tube in fixed relation thereto, a second arm having a portion adapted to receive the tip of a tube extending through the plane of said arm in guiding relation, both of said arms being mounted about a common point for pivotal movement with respect to said frame, a tube with a portion thereof extending downwardly from and in fixed relation to said first arm and having a reduced diameter tip portion at one end thereof, said tip being received in said second arm, means for oscillating said arms about said pivot point, means for reciprocating said first arm to create vertical movement of said tube tip with respect to said second arm, said tube having another end portion adapted for attachment to a pump for aspirating and discharging liquid from the interior of said tube, means for receiving a supply of tip wiping material in ribbon form, said receiving means being associated with said second arm, a takeup spool adapted to receive an end of said ribbon and adapted to be rotated to take up said ribbon, means on said second arm for guiding the path of said ribbon from said ribbon supply receiving means to said takeup spool along a path adjacent said tube tip, said guiding means having portions adapted to urge said ribbon into wiping contact with said tip, and means responsive to relative movement between said second arm and said frame for positively driving said takeup spool, whereby said spool is driven during movement of said second arm about said pivot point.

12. An apparatus as defined in claim 11 wherein said means for driving said takeup spool includes a clutch mechanism adapted to advance said spool in one direction of motion of said second arm and to prevent reverse rotation of said spool during movement of said second arm in the opposite direction.

13. An apparatus as defined in claim 11 in which said means for positively driving said takeup spool include a spool drive gear mounted for rotation with respect to a portion of said second arm, a gear sector fixed with respect to said frame and having a peripheral portion engaged with said drive gear, and a drive shaft extending axially of said drive gear and having a portion engaged in driving relation with said takeup spool.

14. An improved specimen transfer apparatus, said apparatus comprising a liquid transfer unit and a tip wiper unit, said transfer unit including a frame unit and a turntable supported thereon, a container ring and transfer disc mounted on said turntable, said container ring including means for receiving a plurality of containers therein, said transfer disc being received radially of said container ring, a transfer tube having a reduced diameter tip portion on one end thereof and means on the other end thereof for connection to a liquid transfer pump, said tip wiper unit including means for locating the said tip portion of said tube and for guiding said tube for movement between a first operative position in which said tube will aspirate a charge of liquid from said container received in said ring and a second position overlying said transfer disc, from which position said tube will discharge said liquid, means on said tube guiding means for receiving a supply of an absorbent wiping material in ribbon form and for taking up said material, means defining a path along which said material will move between said supply means and said takeup means, said path defining means including means spaced closely apart from said tip for urging said ribbon into wiping contact with said tip, cooperating means responsive to movement of said locating and guiding means for driving said takeup means and means for maintaining said material under tension while said material moves along said path, whereby in use, liquid is first withdrawn from said sample container, said tip is then wiped by movement of said material from said supply means toward said takeup means, and said sample is thereafter discharged into said transfer disc.

15. A method of wiping the tip of a sample aspirating and dispensing tube, said method comprising inserting said tube tip within a sample container, drawing an aliquot portion of said sample into the interior of said tube, withdrawing said tube from said container, supporting said tip portion against deflection and moving said tip portion of said tube toward a container into which said liquid is to be discharged, advancing two continuous ribbons of absorbent material from a supply station to a takeup station in response to movement of said tip support while guiding selected portions of said ribbons generally along the movement path of said tip and urging them into wiping contact with said tip during movement thereof toward said container into which said liquid is to be discharged.

* * * * *